US006545242B1

(12) United States Patent
Butler (10) Patent No.: US 6,545,242 B1
(45) Date of Patent: Apr. 8, 2003

(54) APPARATUS AND METHOD FOR REMOVING A NEEDLE FROM A SYRINGE

(75) Inventor: William F. Butler, Marietta, GA (US)

(73) Assignee: Q Care International LLC, Marietta, GA (US)

( * ) Notice: Subject to any disclaimer, the term of this patent is extended or adjusted under 35 U.S.C. 154(b) by 0 days.

(21) Appl. No.: 09/971,302

(22) Filed: Oct. 4, 2001

(51) Int. Cl.[7] .......................... B23K 11/22; A61M 5/32; A61G 12/00
(52) U.S. Cl. .............................. 219/68; 83/944; 604/110
(58) Field of Search ............................ 219/68; 604/110; 83/944

(56) References Cited

U.S. PATENT DOCUMENTS

| | | | |
|---|---|---|---|
| 4,417,460 A | * | 11/1983 | Moriconi |
| 4,628,169 A | | 12/1986 | Ch'ing-Lung |
| 4,786,280 A | * | 11/1988 | Maeda ....................... 604/110 |
| 4,877,934 A | | 10/1989 | Spinello |
| 5,067,223 A | * | 11/1991 | Bruno |
| 5,091,621 A | | 2/1992 | Butler |
| 5,264,675 A | | 11/1993 | Butler |
| 5,268,549 A | | 12/1993 | Butler |
| 5,288,964 A | * | 2/1994 | Walker et al. ................ 219/68 |
| 5,545,869 A | * | 8/1996 | Piva ............................ 219/68 |
| 5,736,706 A | | 4/1998 | Butler |
| 5,979,275 A | * | 11/1999 | Waluda |
| 6,036,671 A | * | 3/2000 | Frey ........................... 604/110 |

* cited by examiner

Primary Examiner—Geoffrey S. Evans
(74) Attorney, Agent, or Firm—Kilpatrick Stockton LLP (57) ABSTRACT

A method and apparatus for removing the needle portion of a hypodermic syringe and simultaneously sterilizing and destroying the needle portion of a hypodermic syringe, thereby eliminating the risk of infection by microorganisms that may be present in or on the needle. When a syringe is inserted into the apparatus, the needle is heated to a temperature sufficient to melt or at least soften the needle, and sufficient to inactivate any virus, bacteria, yeast, or other microorganism remaining on or within the needle. The needle also is cur at the location of melting so that the needle is removed from the remaining portion of the syringe. The heating and cutting elements are part of a disposable cartridge, which also contains the cut-off needle portions.

29 Claims, 7 Drawing Sheets

Fig_1

Fig. 2

Fig_3

_Fig_ 5

_Fig_ 6

Fig_7

APPARATUS AND METHOD FOR REMOVING A NEEDLE FROM A SYRINGE

TECHNICAL FIELD

This invention relates to a method and apparatus for destroying the needle portion of a syringe. In particular, the present invention relates to a method and apparatus that heats, sterilizes and severs the needle portion of a syringe after the needle has been used on a patient.

BACKGROUND OF THE INVENTION

The threat of infectious diseases, in particular AIDS and hepatitis B, is very prevalent today in hospitals and doctors' offices as a result of the use of hypodermic syringes. The Centers for Disease Control in Atlanta has extensively studied accidental syringe sticking incidents and have logged where most of the accidents occur and to whom. The Centers' records indicate that nurses experience more incidents than most other medical personnel.

Recovering the needle after use, using the plastic tip cover provided with the syringe, is not an effective solution because a person may be stuck while attempting to place the cover on the needle. For that reason, medical professionals are prohibited from recapping syringes after use and instead must place used syringes in an approved disposal such as a sharps container. So-called safety needles having a slideable housing to cover the needle after use have been proposed, but have not found widespread acceptance.

The prior art includes the apparatus disclosed in U.S. Pat. No. 4,628,169, which describes an apparatus for melting only the tip of the needle, with the remainder of the metal on the syringe being detached by a separate operation. The remaining metal portion may still be contaminated. That apparatus still leaves the possibility of the person collecting the remaining needle portion being exposed to microorganisms. Also, any infectious fluids are still available to flow out of the now-open plastic portion of the syringe.

U.S. Pat. No. 4,877,934 discloses a needle destroying apparatus using converging electrodes to destroy the needle. However, the burnt needle tends to bend and lose contact with an electrode during operation, and the burnt needles tend to collect on the bottom electrode of that apparatus.

U.S. Pat. No. 5,736,706 discloses apparatus for removing syringe needles using a needle carriage that must be rotated from a loading position to a cut-off position to sever and remove the needle from the syringe.

What is needed is an improved needle removal apparatus that is easy to operate and will reliably remove and contain the needle without risk of sticking. What is further needed is an apparatus that can be used in a clinical environment for long periods of time without requiring disassembly for servicing or cleaning

SUMMARY OF THE INVENTION

Stated generally, the present invention is an apparatus and method for destroying a syringe needle by heating the needle to the melting temperature and simultaneously severing the needle from the plastic syringe. More particularly, the invention comprises a housing and a needle cartridge that receives a needle in a loading position. When a needle is inserted into the housing, the needle cartridge is retracted to a cut-off position. At the cutoff position, two opposing contact surfaces pinch the needle and electrically connect the needle to an electrical power source such as a battery. Current flows through the contact surfaces and the needle, thereby melting a portion of the needle. This retracting motion of the needle cartridge also causes the contact surfaces to sever the needle at the melted portion, so that the severed portion of the needle falls into a waste compartment in the housing. The apparatus preferably includes a layer of fire-retardant material that the needle penetrates to engage the needle cartridge, to prevent sparks from escaping the apparatus as the needle is melted and severed. When the syringe is removed from the needle cartridge, the needle cartridge returns to the initial loading position.

The needle cartridge is removable from the housing for suitable disposal after destroying a predetermined number of needles. The severed needle portions remain within the needle cartridge during and after such removal, and thus are not exposed to contact by the waste handlers. The replacement needle cartridge includes new contact surfaces for pinching and melting needles, so that the contact surfaces should not require servicing during normal operation.

It is therefore, an object of the present invention to provide a safe, low cost, efficient and easy-to-use device for sterilizing and destroying the metal needle of a hypodermic syringe, thereby killing any infectious microorganism that may be present in or on the needle.

DETAILED DESCRIPTION OF PREFERRED EMBODIMENTS

The present invention is a method and apparatus for removing and safely discarding the needle portion of a hypodermic syringe. The present invention is, in part, an apparatus that is capable of simultaneously sterilizing and removing the needle portion of a hypodermic syringe and hereby eliminating the risk of infection by a microorganism that may be present in or on the needle.

When a syringe is inserted into the apparatus described herein, a portion of the needle adjacent the plastic barrel of the syringe is heated to a temperature of at least 1,750° C. This temperature is capable of inactivating any virus, bacteria, yeast, or other microorganism remaining on or within the needle. In addition to being heated to the melting point, the needle metal is sheared at the melted region so that the needle is removed from the remaining portion of the syringe.

Referring now to FIGS. 1–3, 110 denotes generally a needle removal and disposal apparatus according to the present invention, and including a housing 111 and a needle cartridge 112 removably received within the open upper end 111a of the housing. The housing and cartridge are made of any suitable material such as metal, plastic or the like, so long as that material is capable of maintaining structural integrity if exposed to sparks caused by the melting needle as described below. The needle cartridge 112 is made so that it can be withdrawn from the open upper end of the housing 111 and disposed of at the end of its useful lifetime. Because the needle cartridge of the disclosed embodiment is meant to be disposable in normal use, it is preferred that the materials of that cartridge be chosen with the cost of replacement in mind.

The housing preferably includes a base 116 having a substantially flat bottom surface, thus allowing the apparatus to be placed upright on a table, counter top, or other similar surface. The base also may be adapted for mounting on a wall. The housing has a front wall 118, a rear wall 120, and side walls 122 defining a generally hollow interior 126 open at the upper end 111a to receive the needle cartridge 112, which is removably received within the hollow interior of the housing. The needle cartridge 112 includes a collar 113 that rests on the upper end of the housing 111, and a needle removal unit 114 retained within the collar for vertical movement relative to the collar and the housing, as indicated by arrow 115 in FIG. 2. The needle removal unit is located within the housing 111 on top of a compression return spring 140, FIG. 2. When no downward force is applied to the needle removal unit, the compression spring 140 maintains that unit in the upper loading position shown in FIGS. 1–3. A waste compartment 128 generally comprising a hollow chamber, is located within a lower portion of the needle removal assembly. The upper portion of the waste compartment is open to receive cut-off needles, as described below.

A dish 136 for receiving a needle to be removed is provided in the upper end 134 of the needle removal assembly 114. The dish 136 is in the shape of a cone, having a wide upper end to accept the needle end of a hypodermic syringe and tapering down to a small opening 137, FIGS. 1 and 5, dimensioned to receive only the metal needle portion of a hypodermic syringe.

Figure 4:
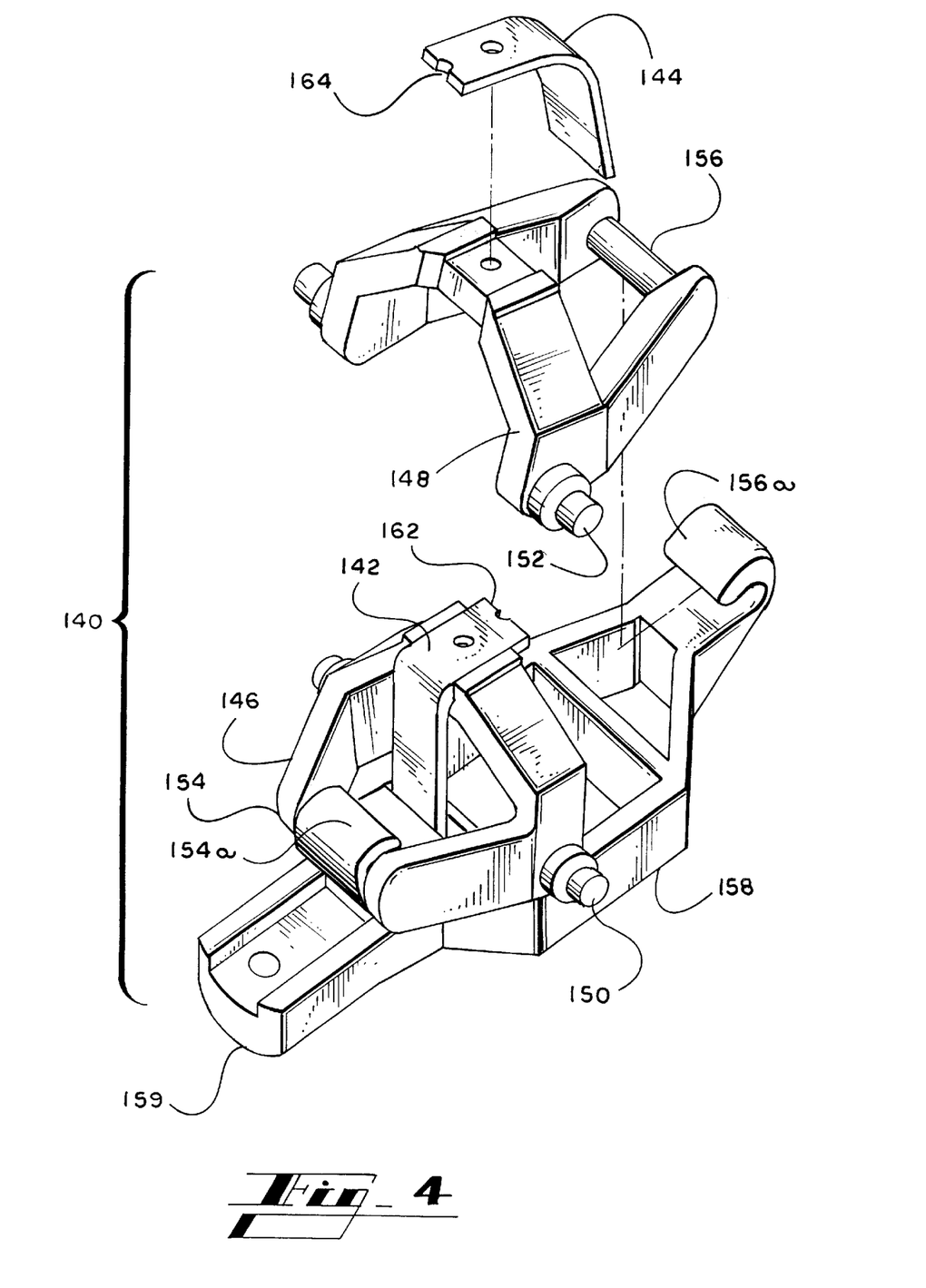
FIG. 4 shows an enlarged and expanded pictorial view of the needle cutting elements in the embodiment of FIG. 1.

Secured within the needle removal unit 114, immediately below the opening 137 at the lower end of the of the dish 136, is a needle contact and cutting assembly 140 best seen in FIGS. 4–6. That assembly has a pair of contact blades 142 and 144, each being formed of electrically conductive material such as steel. Each blade 142 and 144 is mounted at first ends of paired L-shaped levers forming yokes 146 and 148. The yokes are pivotably supported by axles 150 and 152, each mounted within the needle removal unit 114 so as to move up and down with the needle removal unit.

The second ends 154 and 156 of the yokes 146 and 148 are engaged by fingers 154a and 156a of the yoke key 158, located below the yokes. The yoke key 158 is within the needle removal unit 114 but has an extension 159 protruding through a slot in the side of that unit to fit within a mating recess 160 formed on the inside wall of the collar 113. The yoke key 158 thus remains stationary and pivots the yokes 146 and 148 on their axes 150 and 152 when the needle removal unit 114 moves within the collar.

Figure 6:
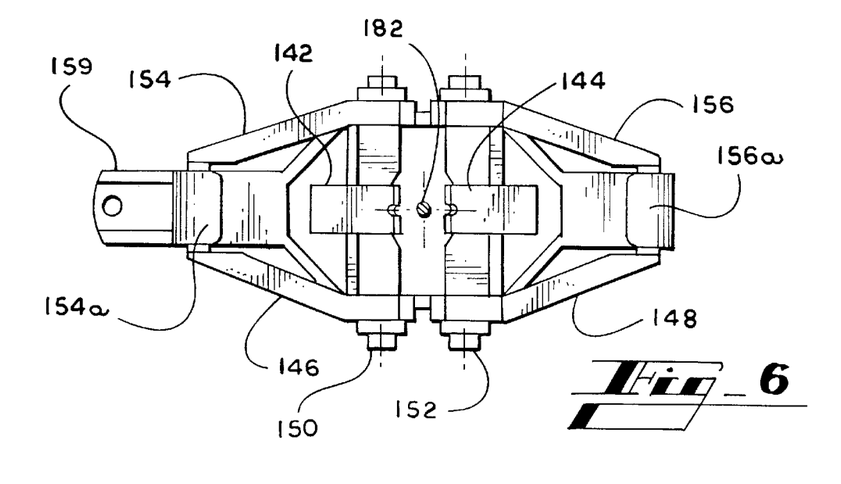
FIG. 6 is a top view in assembly, of the needle cutter as shown in FIG. 4, showing a syringe needle positioned for severing.

Sharpened inner edges 162 and 164 on the contact blades 142 and 144 extend directly under and on opposite sides of the opening 137 in the dish 136, and those inner edges may be notched at the point of contact with a needle 182, FIG. 6, placed between the contact blades. Electrical connector tabs 165a, 165b on the ends of the contact blades opposite the inner edges are electrically connected by wires 166a, 166b (FIG. 7) to a power connector 167 located on a lower portion of the needle cartridge 112 so as to contact mating terminals of a connector 168 within the housing 111. The connectors 167 and 168 are housed within the power connection 170, FIG. 2, for physical isolation from other components when the needle cartridge is inserted within the upper end of the housing.

Figure 1:
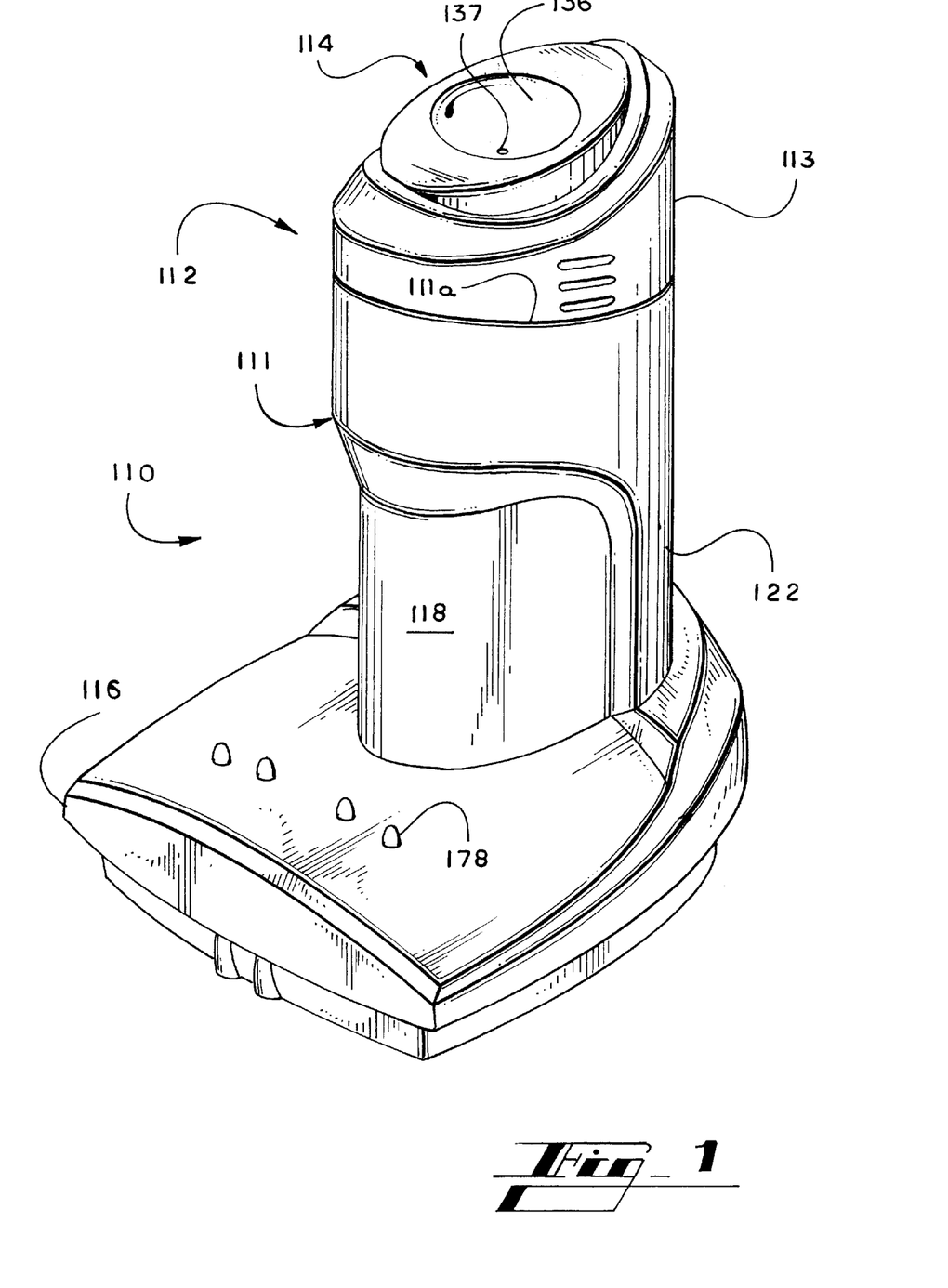
FIG. 1 is a pictorial view of syringe needle destroying apparatus according to a preferred embodiment of the present invention.
Figure 2:
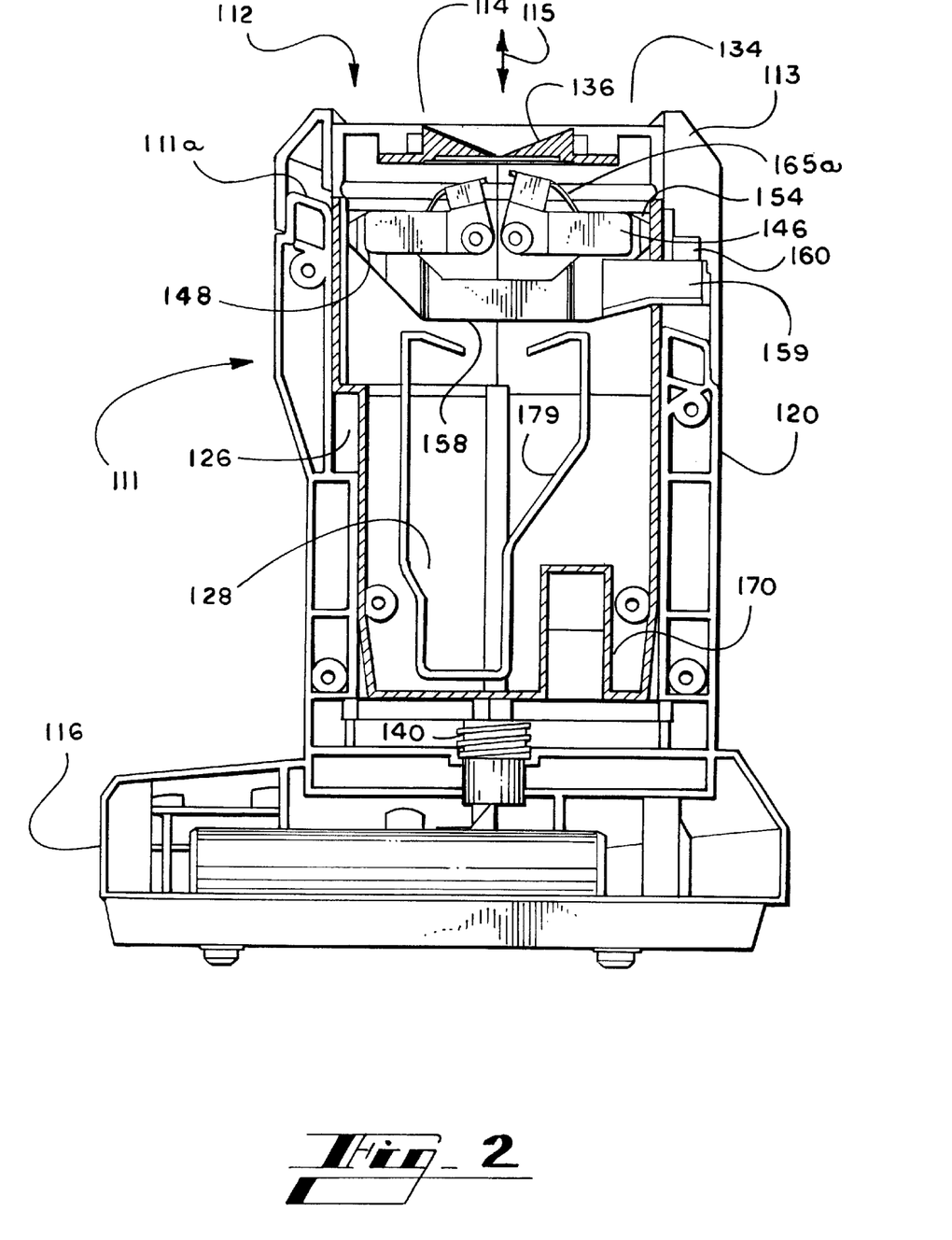
FIG. 2 is a sectional side elevation section view of the apparatus shown in FIG. 1.
Figure 3:
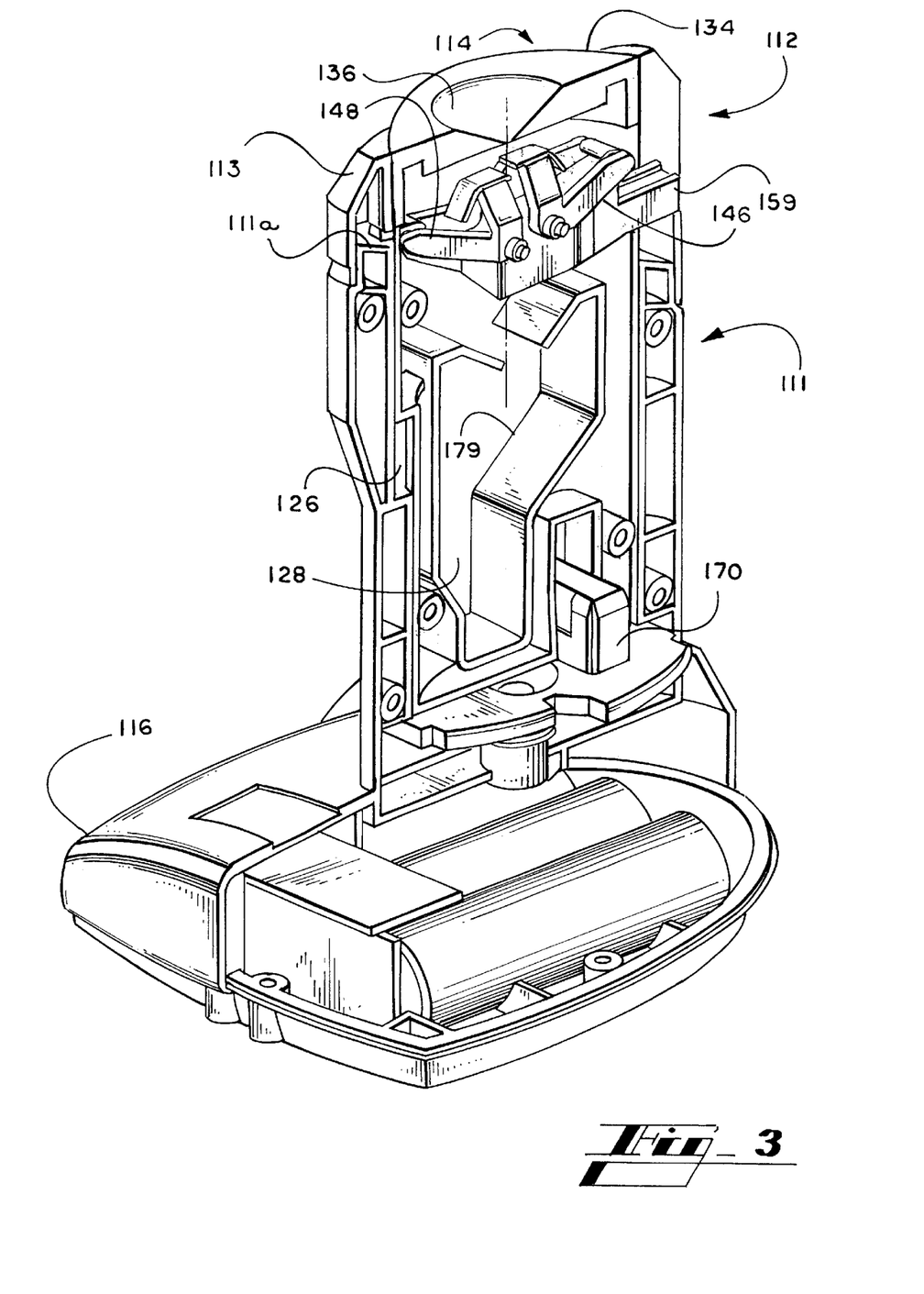
FIG. 3 is a pictorial view of the apparatus as in FIGS. 1 and 2, shown partially broken away for illustration.

The power connector 168 is connected to a power source such as the rechargeable battery 172 located in the base 116 of the housing 111. The battery 172 is charged by plug connection to an external transformer 174 through a control circuit 176 within the base. A circuit breaker is incorporated in the electric circuit including the battery and the control blades. The circuit breaker will trip to open the power circuit in response to a current exceeding a normal amount for the brief duration required to melt the needle of a syringe. Such excessive current might be caused, for example, by insertion through the opening 137 of a metal object more durable than the conventional needle. A reset control for the circuit breaker is located on the base of the housing. A fuse 173 or circuit breaker in the power circuit to the power connector provides added protection against prolonged excess current.

Figure 7:
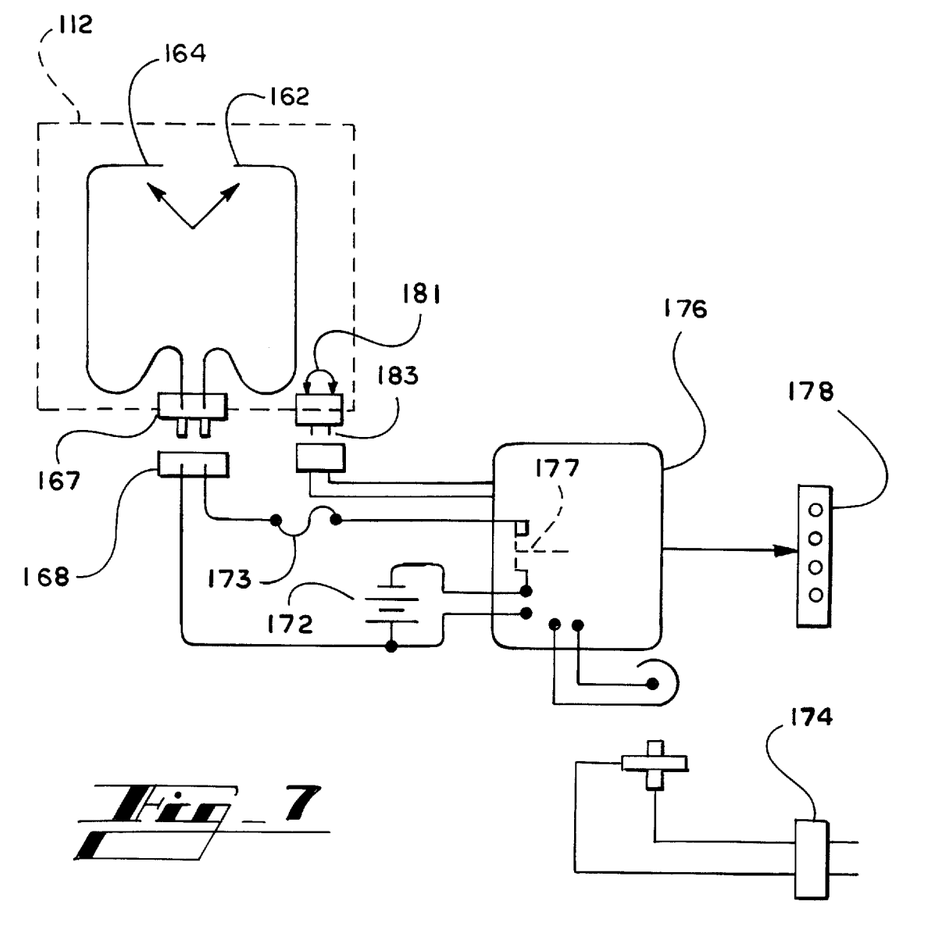
FIG. 7 is a schematic wiring diagram for the embodiment of FIG. 1.

One side of the power circuit from the battery 172 to the power connector goes through the control circuit 176 and includes a switch 177 schematically shown in FIG. 7. The control circuit 176 also connects to a fusible link 181 in the needle removal unit 112, by a second pair of mating connectors 183 on a lower portion of the needle cartridge and within the housing 111. The fusible link 181 is selected to blow in response to a relatively low-power signal current, which the fusible link receives from the control circuit 176 when a fresh needle cartridge is inserted into the housing 111. The momentary current flow through the circuit including the fusible link operates a logic circuit within the control circuit, signifying to that logic circuit that the needle removal apparatus 110 has a fresh needle cartridge, whereupon the logic circuit resets a counter within the control circuit that keeps track of the number of times the previous needle cartridge drew a needle-melting current from the battery. Because the control circuit looks for an intact fusible link 181 when a needle cartridge is installed, the apparatus 110 will not operate if a needle cartridge is removed and later reinstalled within the apparatus.

The control circuit 176 is connected to operate four LEDs 178 on the base 116. Those LEDs indicate functions of the control circuit, which by way of example are: a green LED, indicating the unit is charged and ready to function; a yellow LED indicating the battery 172 is low and requires connection to the charger; a red LED indicating the apparatus is turned off and will not cut needles (for example, because the battery is too low or the cartridge 112 is full and needs replacing); and an orange LED that commences flashing at a predetermined number of cuts, indicating the needle cartridge is nearing capacity. The orange LED will stop flashing and the red LED turns on when the counter of the control circuit 176 registers maximum capacity. When the needle cartridge 112 is replaced with a fresh cartridge containing an intact fusible link 181, the control circuit turns off the red and orange LEDs and turns on the green LED, indicating the unit is again ready to cut needles.

A layer of fire-resistant material 180 (FIG. 5) easily penetrated by a needle is located between the opening 137 of the dish 136 and the first contact blade 142. The material 180 preferably is woven so as to be repeatedly penetrable by needles without cutting or otherwise damaging the material. A fire-resistant fiber such as Nomex® or the like is used for the material 180, in a preferred embodiment of the invention.

Figure 5:
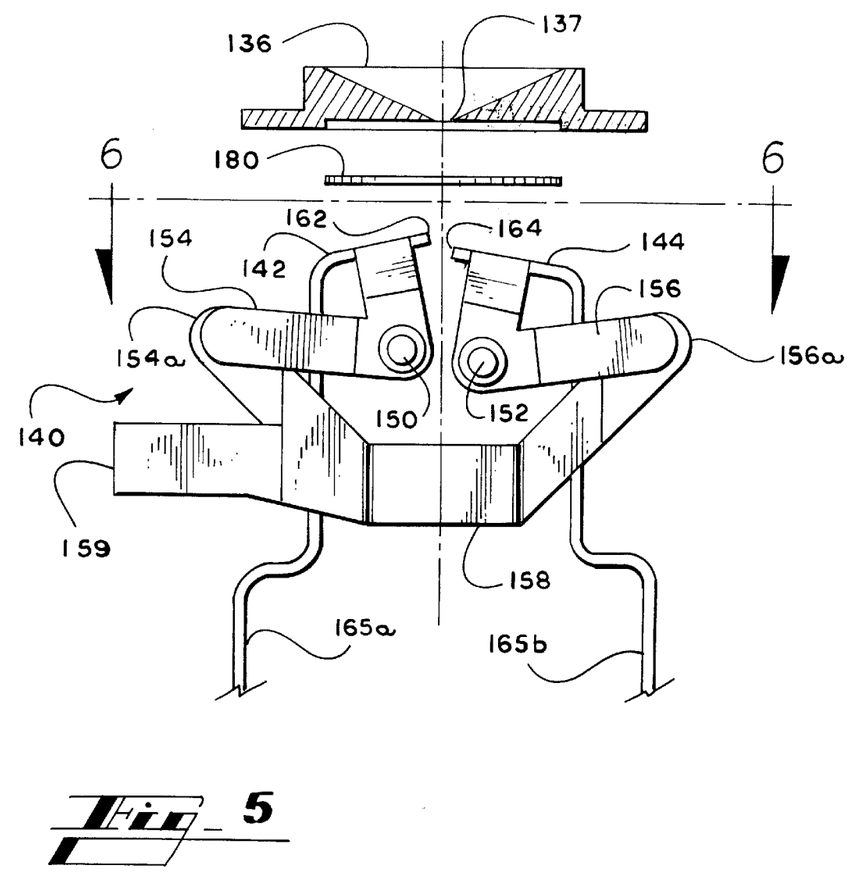
FIG. 5 is a side view of the elements shown in FIG. 4, together with the needle-receiving cup.

In operation of the apparatus 110, a hypodermic syringe is inserted, needle first, into the dish 136 in the needle cartridge with the needle cartridge in the loading position as shown in FIGS. 2 and 5. The needle 182 is fully inserted through the opening 137 at the bottom of the dish until the neck and shoulder portions of the syringe contact the bottom of the dish 136 and can be inserted no further. When the hypodermic needle 182 is fully inserted, the needle penetrates the layer of material 180 to extend beyond and between the sharpened inner edges 162 and 164 of the first and second contact blades 142 and 144.

With the needle remaining fully inserted, the syringe is pushed down against the dish 136 in order to depress the needle removal unit 114 into the cut-off position. The introduction of downward force exerted on the needle removal unit 114 overcomes the resistance force of the compression spring 140, so that the needle removal unit moves downwardly within the collar 113 and housing 111. As the needle removal unit moves downwardly, the yoke key 158 pivots the yokes 146 and 148 on the axles 150 and 152, causing the inner edges 162 and 164 of the contact blades to engage opposite sides of the needle 182 immediately below the fire-resistant layer 180 beneath the bottom of the dish 136.

The axle 152 of the yoke 148 is mounted slightly below the corresponding axle 150 of the other yoke 146, as best seen in FIG. 5. As a result, the edge 164 of the contact blade 144 contacts the needle 182 at a small offset from the edge 162 of the other blade 142. When the needle is thus contacted by both contact blades as the needle removal unit 114 is depressed to the cut-off position, an electrical circuit is formed including the first and second contact blades and that part of the metal needle between the contact blades. Electrical current flowing through the circuit is of sufficient amperage to melt the metal portion of the needle between the first contact blade 142 and second contact blade 144. The sharpened edges of the first and second contact blades pinch the melted needle between the contact blades, shearing the melted needle at the pinch point so that the severed portion of the needle falls downwardly into the waste compartment 128, FIG. 2. The baffle plate 179 in the needle cartridge helps guide the severed needles into that compartment. The electrical circuit is interrupted when the needle is melted and severed at the pinch point, and the hypodermic syringe may then be removed from the dish 136 and placed elsewhere for appropriate disposal. Removing the syringe from the dish 136 removes the downward force on the needle removal unit 114 so that the compression spring 140 returns the needle removal unit to the loading position.

The diameter of the opening 137 in the dish 136 can be sized to accept any conventional gauge stainless steel needles therethrough while blocking entry of the plastic barrel portion of the syringe. The remaining stump of the melted and severed needle typically extends only about ⅛ inch below the barrel portion and lacks a sharp point, thus presenting no needle-sticking hazard. Moreover, the high temperature reached to melt the steel needle should render harmless any infectious organisms that may have been present on or within the needle. The layer of fire-resistant material 180 prevents sparks or flames from entering the dish 136 through the opening 137 as the contact blades engage the needle.

The needle cartridge 112 and its components are intended to be disposable upon removal from the housing. The needle cartridge 112 thus will be periodically removed for disposal and replaced with a fresh cartridge. The severed needles remain enclosed within the removed needle cartridge, as that cartridge is disposed in an appropriate manner.

Contacting needles with the sharp edges of the two opposed contact blades as disclosed herein help make a positive electrically-conductive contact with the needle, cutting through any nonconductive coating such as medical epoxy that may cover the outside surface of the needle. Moreover, pressing both contact blades against opposite sides of the needle avoids bending the needle, which might otherwise hinder melting and subsequent dropping of the cutoff needle segment.

Because the sharp edges of the contact blades 142 and 144 are exposed to elevated temperature and electrical arcing each time a needle is melted and cut off, the blades must be replaced after a number of needle-removal operations so as to maintain effective operation of the apparatus. The blades are replaced by removing and disposing of the entire needle cartridge 112, which also disposes of the removed needles accumulated in the waste compartment 128. To assure timely replacement of the needle cartridge 112, the counter within the control circuit 176 increments a count in response to each time the contact blades establish current flow through a needle. When the counter is incremented to a predetermined number, the switch 177 associated with the control is opened so as to prevent further operation of the apparatus until the needle cartridge is replaced. The control circuit at that time illuminates the red LED on the base 116, indicating that the apparatus will not operate until the needle cartridge is replaced. Merely removing and reinstalling the used needle cartridge will not reset the counter or reactivate the apparatus, because the fusible link 181 in that needle cartridge now lacks an intact fusible link 181 required to tell the control circuit that a fresh needle cartridge has been installed.

In a preferred embodiment of the present invention, the apparatus is inactivated in response to 200 needle removals. The orange LED commences flashing when 180 needle removals occur, indicating the needle cartridge will soon require replacement. It should be understood that these counts are not critical aspects of the invention.

Figure 8:
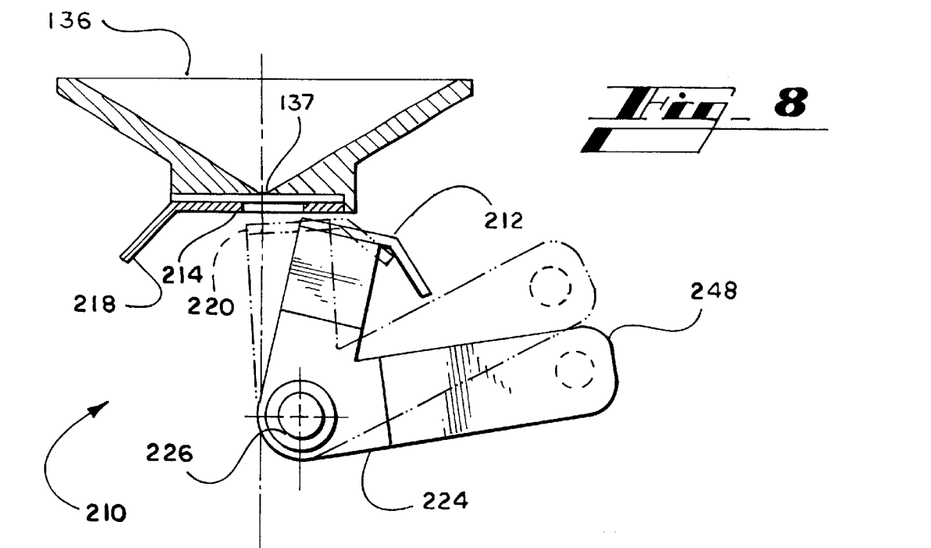
FIG. 8 is an elevation view showing a modification of the needle contact and cutting assembly in the present invention.
Figure 9:
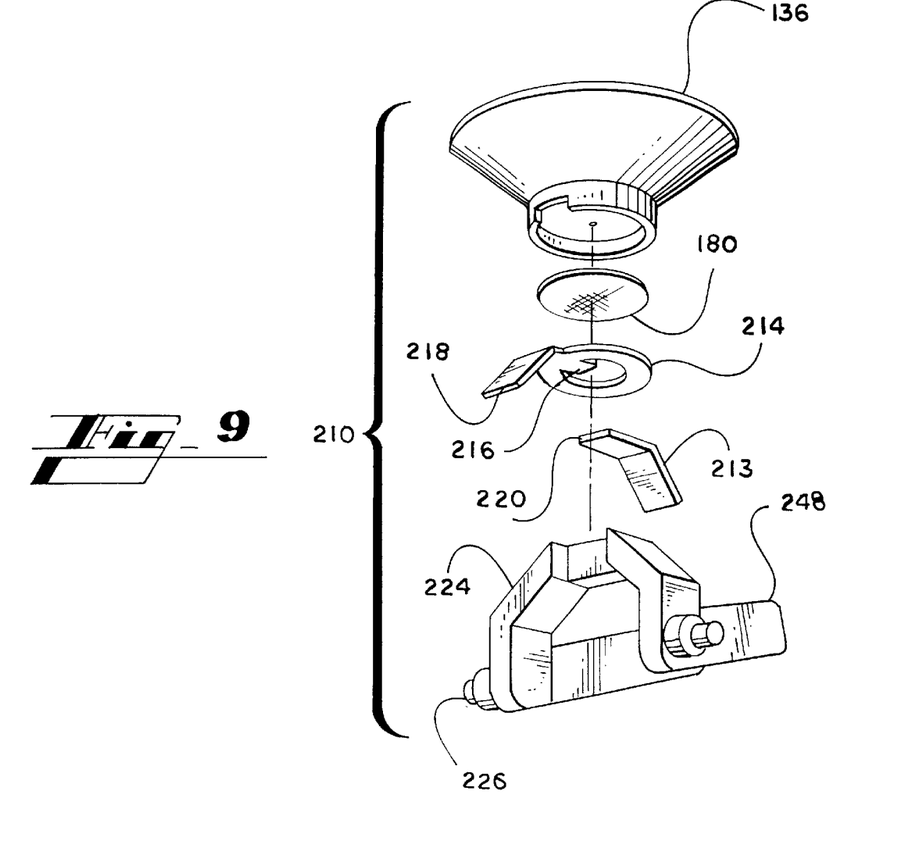
FIG. 9 is an exploded view of the modification shown in FIG. 8.

FIGS. 8 and 9 show an alternative embodiment of apparatus according to the present invention, in which the needle contact and cutting assembly 210 uses a single movable contact blade 212 and a fixed contact blade 214 instead of the first and second movable blades in the previously-described embodiment. The fixed contact blade 214 is secured within the needle cartridge, immediately below the opening 137 at the bottom of the dish 136. The fixed contact blade 214 is formed of electrically conductive material and has an annular shape surrounding the opening 137. A sharpened inner edge 216 of the fixed contact blade extends directly under the smaller opening 137, and a tab 218 on the fixed contact blade is electrically connected by a wire to a first terminal of the battery or other suitable power supply as previously described. The layer of fire-resistant material 180 is disposed between the opening 137 of the dish 136 and the fixed contact blade 214.

The movable contact blade 212 is located at one end of a yoke 224 pivotably supported on the axle 226. That movable contact blade is connected by a wire to a second terminal of the battery or other power supply and has an outer sharpened edge 220 located immediately below the fixed contact blade 214. The other end of the yoke 224 has a finger 248 extending for engagement with a fixed element of the housing within which the needle cartridge containing the assembly 210 is received, in the manner of the extension 159 of the yoke key 158 in the embodiment described above.

When a hypodermic syringe is inserted needle-first into the dish 136 in the embodiment shown in FIGS. 8 and 9, the needle penetrates the layer of material 180 to extend beyond and alongside the sharpened inner edge 216 of the fixed contact blade 214. With the needle remaining fully inserted, downward force is applied to the syringe to move the needle cutting assembly 210 downwardly into the cut-off position in opposition to the resistance force of the compression spring 140, mentioned above. As the needle cutting assembly 210 moves downwardly, the finger 248 contacts a fixed element of the housing, pivoting the yoke 224 on the axle 226 and causing the sharpened inner edge 220 of the second contact blade 212 to engage the needle and displace the needle into contact with the sharpened inner edge 216 of the fixed contact blade 214.

When the needle is thus contacted by both contact blades as the needle cutting assembly is depressed to the cut-off position, an electrical circuit is formed including the first and second contact blades and the needle portion between the contact blades, and an electrical current flows through the circuit to melt that portion of the needle. The sharpened edges of the first and second contact blades pinch the melted needle between the contact blades, shearing the needle at the pinched point so that the severed portion of the needle falls downwardly into the waste compartment as previously described.

Further details of the embodiment shown in FIGS. 8 and 9 are in Provisional Application No. 60/233,456, the disclosure of which is incorporated herein by reference.

From the foregoing it will be appreciated that the disclosed embodiments of the present invention overcome the drawbacks of the prior art described herein above. While this invention has been described in detail with particular reference to preferred embodiments thereof, it will be understood that variations and modifications can be affected within the spirit and scope of the invention as described herein before and as defined in the appended claims.

What is claimed is:

1. An apparatus for removing the needle portion of a syringe, comprising:
   a housing;
   a needle cartridge for receiving a needle in a loading position, said needle cartridge being selectably movable within said housing from the loading position to a cut-off position;
   first and second contact surfaces associated with said needle cartridge; and
   means operative to move the contact surfaces to contact a needle received in the loading position, in response to moving the needle cartridge to the cut-off position.

2. The apparatus of claim 1, wherein said first and second contact surfaces move to sever a portion of said needle when said needle cartridge is moved to the cut-off position.

3. The apparatus of claim 2, further comprising a waste compartment located within said needle cartridge for receiving the severed portion of said needle, the waste compartment having an upper portion with an opening located generally beneath said contact surfaces.

4. The apparatus of claim 1, further comprising an electrical power supply connected to the contact surfaces and operative to supply sufficient current to melt a portion of the needle when said needle cartridge is in the cut-off position, so that the contact surfaces can sever the molten portion.

5. The apparatus of claim 1, further comprising a spring operatively associated with said housing, and urging said needle cartridge to the loading position in the absence of external force applied to said needle cartridge, so that external force exerted against said needle cartridge compresses said spring, and covers said needle cartridge to move from the loading position to the cut-off position.

6. The apparatus of claim 5, wherein said needle cartridge comprises:
   a port for receiving the needle portion of a syringe in the loading position while preventing entry of a barrel portion from which the needle portion extends; and
   a flame-retarding member disposed between the port and the contact surfaces so as to inhibit sparks from escaping the port as the needle is melted and severed from the barrel portion.

7. Apparatus for removing the needle portion of a syringe, comprising:
   a housing;
   a needle cartridge removably associated with the housing and selectably movable relative to the housing between a loading position and a cutoff position;
   means operatively associated with the needle cartridge and the housing to urge the cartridge to the loading position and responsive to force exerted on the cartridge in opposition to the urging to allow the cartridge to move to the cutoff position;
   the needle cartridge having a port for receiving a needle portion of a syringe along a predetermined path of entry while preventing entry of a barrel portion from which the needle portion extends;
   a pair of contact elements associated with the needle cartridge at one side of the port;
   the contact elements being in mutually opposed relation to each other and in predetermined alignment alongside the entry path as the cartridge is in the loading position;
   a source of electric current connected in circuit with the contact elements; and
   means operative in response to movement of the needle cartridge to the cut-off position to urge at least one contact element into contact with a needle occupying the entry path, whereupon the needle contacts both contact elements so that the contact elements establish a flow of current through a needle portion sufficient to melt the needle portion,
   whereupon the contact elements separate the needle from the barrel of the syringe.

8. Apparatus as in claim 7, wherein the contact elements are offset from each other a distance along the entry path for the needle, so that the current flows through the needle along that distance.

9. Apparatus as in claim 7, wherein:
   the housing is open at an upper end to receive the needle cartridge within the housing;
   the needle receiving port is at an upper end of the needle cartridge so as to receive needles along a substantially vertical entry path including the port; and
   the needle cartridge is movable from the loading position to the cutoff position along a substantially vertical path, so that needles may be inserted into the port irrespective of angular position around the entry path.

10. Apparatus as in claim 7, wherein:
    the removable needle cartridge has a first portion received in stationary relation with the housing, and a second portion selectably movable relative to the first portion and to the housing; and the contact elements move with the second portion to contact a needle in the entry path when the second portion is moved to the cutoff position.

11. Apparatus as in claim 10, further comprising:

an actuating member associated with said at least one contact element in the second portion of the needle cartridge and having an operating member engaging the first portion of the needle cartridge; and the actuating member being operative to move said at least one contact element toward the needle entry path in response to movement of the second portion to the cutoff position.

12. Apparatus as in claim 11, wherein:

both the contact elements are movable relative to the needle entry path in response to the actuating member.

13. Apparatus as in claim 11, wherein:

each contact element is on a separate lever; and each such lever is movable in response to the actuating member so that both contact elements move relative to the needle entry path.

14. Apparatus as in claim 7, wherein:

the source of electric current is in the housing, and further comprising:

electrical conductors in the needle cartridge extending from the contact elements to a connector operative to establish electrical contact with the source in the housing when the needle cartridge is inserted into the housing; and control means responsive to the electrical circuit to count the number of needle removals performed by the needle cartridge.

15. Apparatus as in claim 14, further comprising:

means responsive to a predetermined number of counted needle removals for a needle cartridge to disable operation of the apparatus until the needle cartridge is replaced.

16. Apparatus as in claim 14, wherein:

the needle cartridge includes a memory element having a first state indicating an unused condition and operative to change to a second state in response to inserting the needle cartridge in the housing.

17. Apparatus as in claim 16, wherein:

the control means is responsive to the second state of the memory element to disable operation of the apparatus if a needle cartridge with the memory element in the second state is installed in the housing.

18. Apparatus as in claim 16, wherein:

the control means is responsive to the first state of the memory element, in a needle cartridge installed in the housing, to change the state of that memory element to the second state, so that the needle cartridge thereafter is identifiable as used.

19. Apparatus as in claim 15, wherein:

the needle cartridge includes a memory element having a first state corresponding to an unused condition and operative to change to a second state corresponding to a used condition; and the control means is responsive to the first state of the memory element, in a needle cartridge installed in the housing, to reset the counter so as to enable operation with that needle cartridge, and to change the state of the memory element to the second state so that the needle cartridge is no longer unused.

20. Apparatus as in claim 18, wherein:

the memory element comprises a fusible link in the needle cartridge, and circuit means operatively associating that fusible link with the control means when the needle cartridge is installed in the housing.

21. A needle cartridge for removable association with apparatus for removing the needle portion of a syringe, the needle cartridge comprising:

a first portion receivable in stationary relation with the housing, and a second portion selectably movable between a loading position and a cutoff position relative to the first portion and to the housing;

a port associated with the second portion for receiving a needle portion of a syringe along a predetermined path of entry while preventing entry of a barrel portion from which the needle portion extends;

a pair of contact elements associated with the needle cartridge at one side of the port;

the contact elements being in mutually opposed relation to each other and in predetermined alignment alongside the entry path as the cartridge is in the loading position;

means operative in response to movement of the needle cartridge to the cut-off position to urge at least one contact element into contact with a needle occupying the entry path; and electrical conductors extending from the contact elements to a connection operative to establish electrical contact with a power source associated with the housing within which the needle cartridge is received, so that the contact elements establish a flow of current through a needle portion sufficient to melt the needle portion;

whereupon the contact elements separate the needle from the barrel of the syringe.

22. The needle cartridge as in claim 21, wherein the contact elements are offset from each other a distance along the entry path for the needle, so that the current flows through the needle along that distance.

23. The needle cartridge, as in claim 21, further comprising:

an actuating member associated with said at least one contact element in the second portion of the needle cartridge and having an operating member engaging the first portion of the needle cartridge; and the actuating member being operative to move said at least one contact element toward the needle entry path in response to movement of the second portion to the cutoff position.

24. The needle cartridge, as in claim 23, wherein:

both the contact elements are movable relative to the needle entry path in response to the actuating member.

25. The needle cartridge, as in claim 23, wherein:

each contact element is on a separate lever; and each such lever is movable in response to the actuating member so that both contact elements move relative to the needle entry path.

26. The needle cartridge, as in claim 21, further comprising:

a memory element having a first state corresponding to an unused condition of the needle cartridge and operative to change to a second state corresponding to a used condition; and means communicating the state of the memory element to a control element associated the housing with which the needle cartridge is received.

27. The needle cartridge, as in claim 26, wherein:

the memory element comprises a fusible link in the needle cartridge, and circuit means operatively associating that fusible link with control means associated with the housing within which the needle cartridge is received.

28. A method for removing the needle portion of a syringe, comprising the steps of:

inserting a needle into a needle cartridge in a loading position, the needle cartridge being movably associated with a housing;

moving the needle cartridge from the loading position to a cut-off position;

causing a first contact surface and a second contact surface of the needle cartridge to move into contact with the needle when the needle cartridge is in the cut-off position;

causing an electrical current to pass through the first contact surface and the second contact surface sufficient to melt a portion of the needle contacted by the surface; and severing the needle at the melted portion with the first and second contact surfaces.

29. The method of claim 28 wherein the step of inserting said needle includes inserting said needle into a port in said needle cartridge such that the neck and shoulder portions of said syringe contact said port; and then exerting downward force on said needle cartridge through the neck and shoulder portions of said syringe, so as to move the needle cartridge relative to the housing.

\* \* \* \* \*